US012805846B2

(12) United States Patent
Sornes et al.

(10) Patent No.: US 12,805,846 B2
(45) Date of Patent: Nov. 24, 2026

(54) METHOD AND SYSTEM FOR ESTIMATING MOTION FROM OVERLAPPING MULTILINE ACQUISITIONS OF SUCCESSIVE ULTRASOUND TRANSMIT EVENTS

(71) Applicant: GE Precision Healthcare LLC, Wauwatosa, WI (US)

(72) Inventors: Anders R. Sornes, Oslo (NO); Tore Bjastad, Molde (NO); Bastien Emmanuel Denarie, Nesoya (NO)

(73) Assignee: GE Precision Healthcare LLC, Waukesha, WI (US)

( * ) Notice: Subject to any disclaimer, the term of this patent is extended or adjusted under 35 U.S.C. 154(b) by 772 days.

(21) Appl. No.: 17/196,010

(22) Filed: Mar. 9, 2021

(65) Prior Publication Data

US 2022/0287685 A1 Sep. 15, 2022

(51) Int. Cl.
*A61B 8/00* (2006.01)

(52) U.S. Cl.
CPC .......... *A61B 8/5253* (2013.01); *A61B 8/4483* (2013.01); *A61B 8/461* (2013.01)

(58) Field of Classification Search
CPC ..... A61B 8/5253; A61B 8/4483; A61B 8/461; A61B 8/5223; A61B 8/08; A61B 8/5207; A61B 8/5215
See application file for complete search history.

(56) References Cited

U.S. PATENT DOCUMENTS 10,725,159 B2 * 7/2020 Pellegretti ............ A61B 8/5207
2017/0301094 A1 * 10/2017 Vignon ................ G10K 11/346
(Continued)

FOREIGN PATENT DOCUMENTS

EP 2053420 A1 4/2009
EP 2053420 B1 12/2012

OTHER PUBLICATIONS

"Velocity estimation using recursive ultrasound imaging and spatially encoded signals," In 2000 IEEE Ultrasonics Symposium, Proceedings, an International Symposium (Cat. No. 00CH37121), vol. 2, pp. 1473-1477. IEEE, 2000. (Year: 2000).*
(Continued)

*Primary Examiner* — Joseph M Santos Rodriguez
*Assistant Examiner* — James F McDonald, III
(74) *Attorney, Agent, or Firm* — McAndrews, Held & Malloy, Ltd.; Daniel Bissing; David Bates

(57) ABSTRACT

Systems and methods for estimating motion from overlapping multiline acquisitions of successive transmit events are provided. The method includes receiving a set of receive data points for each of a sequence of partially overlapping transmit beams emitted from transducer elements in multiple directions at a target. The set of receive data points includes a number of receive data point locations overlapping with receive data point locations generated from other transmit beams in the sequence. The method includes compensating each receive data point for a different arrival time. The method includes determining a displacement of the target by comparing components of pairs of co-located receive data points generated in response to different transmit beams. The method includes summing the co-located receive data points into a pixel of a B-mode image and presenting the B-mode image with velocity information based on the determined displacement of the target at a display system.

20 Claims, 3 Drawing Sheets

(56) References Cited

U.S. PATENT DOCUMENTS

| | | | | |
|---|---|---|---|---|
| 2018/0003811 | A1* | 1/2018 | Pellegretti | G01S 7/52077 |
| 2019/0072671 | A1* | 3/2019 | Nikolov | G01S 15/8993 |
| 2019/0090850 | A1* | 3/2019 | Gran | A61B 8/445 |
| 2019/0105016 | A1* | 4/2019 | Jenaro | A61B 8/469 |
| 2020/0138401 | A1* | 5/2020 | Haugaard | A61B 8/5207 |
| 2020/0209371 | A1* | 7/2020 | Meral | G06T 5/002 |

OTHER PUBLICATIONS

Pair, Chambers Paperback Dictionary 355 (2003).*

Bjastad, T. and Torp, H., "Single-Pulse Tissue Doppler Using Synthetic Transmit Beams," IEEE Transactions on Ultrasonics, Ferroelectrics, and Frequency Control, vol. 56, No. 10, Oct. 2009, pp. 2134-2144.

Denarie, B., "Real-time 3-D echocardiography: challenges of parallel transmission and acquisition," Ph.D Thesis, Norwegian University of Science and Technology, NTNU, chapter 4, Nov. 2013, pp. 1-133.

* cited by examiner

METHOD AND SYSTEM FOR ESTIMATING MOTION FROM OVERLAPPING MULTILINE ACQUISITIONS OF SUCCESSIVE ULTRASOUND TRANSMIT EVENTS

FIELD

Certain embodiments relate to ultrasound imaging. More specifically, certain embodiments provide motion estimation from overlapping multiline acquisitions of successive ultrasound transmit events.

BACKGROUND

Ultrasound imaging is a medical imaging technique for imaging organs and soft tissues in a human body. Ultrasound imaging uses real time, non-invasive high frequency sound waves to produce a two-dimensional (2D) image and/or a three-dimensional (3D) image.

Retrospective transmit beamforming (RTB), which may also be referred to as retrospective transmit focusing or true confocal imaging, is a beamforming technique that mitigates the reduction in two-way focusing away from the transmit focus by making use of the large degree of transmit beam overlap in imaged regions. RTB processing may include aligning co-located receive data by compensating for the different delay in transmit wave front arrival times at the target image location for the different transmit events. The aligned events along a particular output direction is subsequently summed to generate a retrospective focused signal where aligned events acquired with differently angled wave fronts is summed with some weighting scheme.

A related technique to RTB is Synthetic Transmit Beamforming (STB) in which receive lines from pairs of neighboring transmit events are combined with a set of weights without any alignment delay. Interpolation of the phases of the weighted sum to the expected phase may be performed if the transmit beam had been at the receive line location.

Further limitations and disadvantages of conventional and traditional approaches will become apparent to one of skill in the art, through comparison of such systems with some aspects of the present disclosure as set forth in the remainder of the present application with reference to the drawings.

BRIEF SUMMARY

A system and/or method is provided for estimating motion from overlapping multiline acquisitions of successive ultrasound transmit events, substantially as shown in and/or described in connection with at least one of the figures, as set forth more completely in the claims.

These and other advantages, aspects and novel features of the present disclosure, as well as details of an illustrated embodiment thereof, will be more fully understood from the following description and drawings.

DETAILED DESCRIPTION

Figure 1:
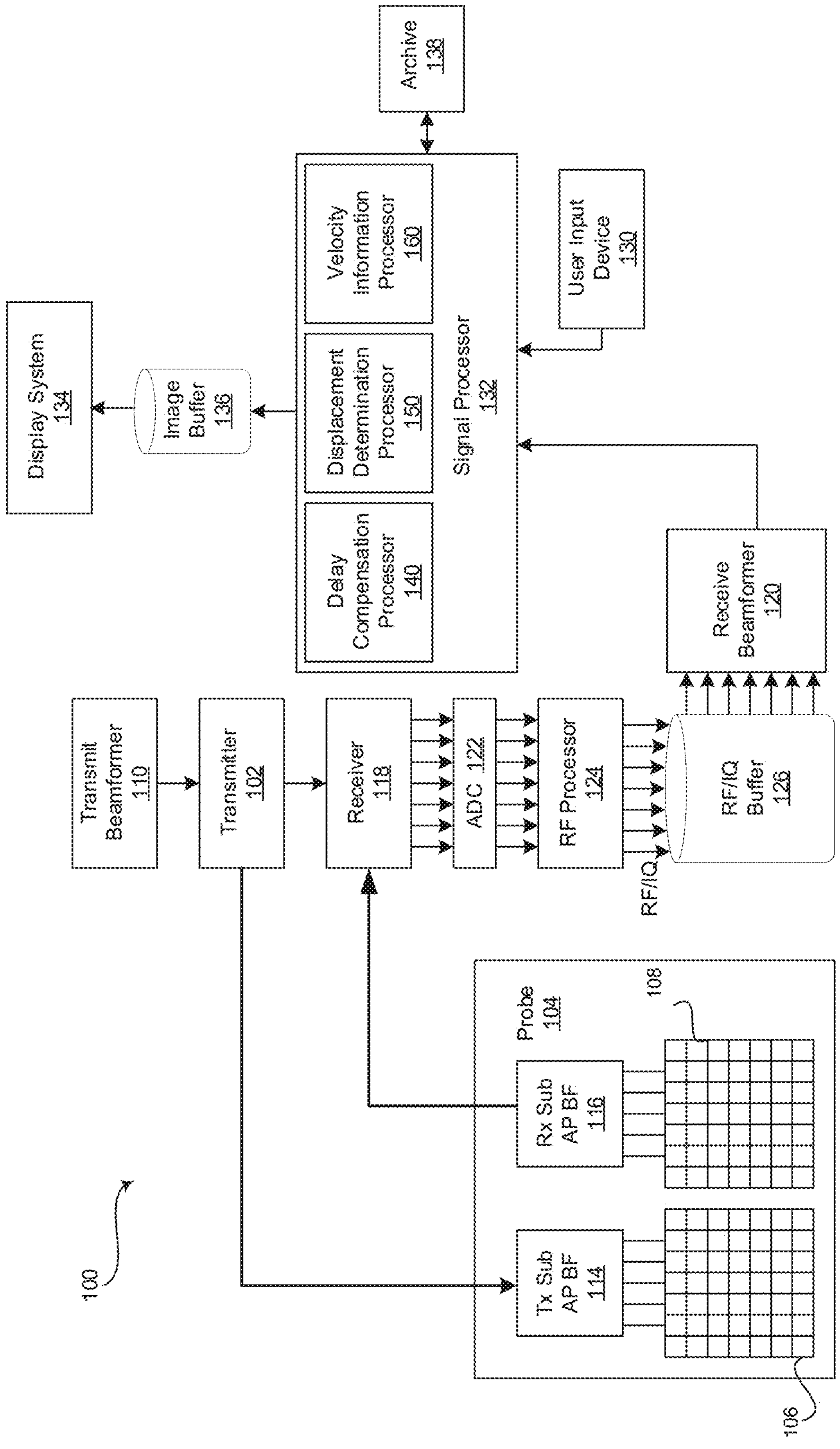
FIG. 1 is a block diagram of an exemplary ultrasound system that is operable to provide motion estimation from overlapping multiline acquisitions of successive ultrasound transmit events, in accordance with various embodiments.

Certain embodiments may be found in a method and system for estimating motion from overlapping multiline acquisitions of successive ultrasound transmit events. More specifically, in Retrospective Transmit Beamforming (RTB), a multitude of overlapping/co-located receive data points from successive transmit beams in an ultrasound scan may be recorded and combined into an output grid synthetic retrospectively focused transmit beams. In each direction, the RTB-delay corrected receive data point components to be summed may also provide an estimate of the local velocity of tissue by calculating the phase of the correlation of the aligned receive data points for successive transmit beam directions. The RTB delay alignment compensates for the registration differences due to transmit wave front location.

Aspects of the present disclosure provide an estimation technique correlating co-located RTB-delay corrected multiline acquisition receive data points from different transmit beams of equivalent transmit-receive geometry. Various embodiments have the technical effect of using RTB-delay compensated co-located receive data points from a manifold of successive partially overlapping transmit beams in order to calculate tissue velocity and or slow flow velocities in the entirety of a B-mode image using the normal acquisition of a single-fire-per-direction B-mode acquisition with RTB. Certain embodiments have the technical effect of performing estimates from receive data points that are corrected for the transmit wave front and that there are far larger "packet size" in that there are more co-located MLAs from a greater number of transmit events at a distance from the focus. Aspects of the present disclosure provide the technical effect of producing velocity estimates of tissue or flow as a by-product of performing regular B-mode imaging with state-of-the-art retrospective transmit beamforming. The velocity information may be used in tissue velocity imaging (TVI), as an input to aid subsequent speckle tracking, and the like.

The foregoing summary, as well as the following detailed description of certain embodiments will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or a block of random access memory, hard disk, or the like) or multiple pieces of hardware. Similarly, the programs may be stand alone programs, may be incorporated as subroutines in an operating system, may be functions in an installed software package, and the like. It should be understood that the various embodiments are not limited to the arrangements and instrumentality shown in the drawings. It should also be understood that the embodiments may be combined, or that other embodiments may be utilized and that structural, logical and electrical changes may be made without departing from the scope of the various embodiments. The following detailed description is, therefore, not to be taken in a limiting sense, and the scope of the present disclosure is defined by the appended claims and their equivalents.

As used herein, an element or step recited in the singular and proceeded with the word “a” or “an” should be understood as not excluding plural of said elements or steps, unless such exclusion is explicitly stated. Furthermore, references to “an exemplary embodiment,” “various embodiments,” “certain embodiments,” “a representative embodiment,” and the like are not intended to be interpreted as excluding the existence of additional embodiments that also incorporate the recited features. Moreover, unless explicitly stated to the contrary, embodiments “comprising,” “including,” or “having” an element or a plurality of elements having a particular property may include additional elements not having that property.

Also as used herein, the term “image” broadly refers to both viewable images and data representing a viewable image. However, many embodiments generate (or are configured to generate) at least one viewable image. In addition, as used herein, the phrase “image” is used to refer to an ultrasound mode such as B-mode (2D mode), M-mode, three-dimensional (3D) mode, CF-mode, BSI mode, 3DCF mode, PW Doppler, MGD, and/or sub-modes of B-mode and/or CF such as Volume Compound Imaging (VCI), Shear Wave Elasticity Imaging (SWEI), TVI, Angio, B-flow, BMI, BMI Angio, and in some cases also MM, CM, TVD, CW where the “image” and/or “plane” includes a single beam or multiple beams.

Furthermore, the term processor or processing unit, as used herein, refers to any type of processing unit that can carry out the required calculations needed for the various embodiments, such as single or multi-core: CPU, Accelerated Processing Unit (APU), Graphics Board, DSP, FPGA, ASIC or a combination thereof.

It should be noted that various embodiments described herein that generate or form images may include processing for forming images that in some embodiments includes beamforming and in other embodiments does not include beamforming. For example, an image can be formed without beamforming, such as by multiplying the matrix of demodulated data by a matrix of coefficients so that the product is the image, and wherein the process does not form any “beams”. Also, forming of images may be performed using channel combinations that may originate from more than one transmit event (e.g., synthetic aperture techniques).

In various embodiments, ultrasound processing to form images is performed, for example, including ultrasound beamforming, such as receive beamforming, in software, firmware, hardware, or a combination thereof. One implementation of an ultrasound system having a software beamformer architecture formed in accordance with various embodiments is illustrated in FIG. 1.

FIG. 1 is a block diagram of an exemplary ultrasound system 100 that is operable to provide motion estimation from overlapping multiline acquisitions of successive ultrasound transmit events, in accordance with various embodiments. Referring to FIG. 1, there is shown an ultrasound system 100. The ultrasound system 100 comprises a transmitter 102, an ultrasound probe 104, a transmit beamformer 110, a receiver 118, a receive beamformer 120, a RF processor 124, a RF/IQ buffer 126, a user input device 130, a signal processor 132, an image buffer 136, a display system 134, and an archive 138.

The transmitter 102 may comprise suitable logic, circuitry, interfaces and/or code that may be operable to drive an ultrasound probe 104. The ultrasound probe 104 may comprise a two dimensional (2D) array of piezoelectric elements or may be a mechanical one dimensional (1D) array, among other things. The ultrasound probe 104 may comprise a group of transmit transducer elements 106 and a group of receive transducer elements 108, that normally constitute the same elements. In certain embodiments, the ultrasound probe 104 may be operable to acquire ultrasound image data covering at least a substantial portion of an anatomy, such as a heart, a fetus, or any suitable anatomical structure.

The transmit beamformer 110 may comprise suitable logic, circuitry, interfaces and/or code that may be operable to control the transmitter 102 which, optionally through a transmit sub-aperture beamformer 114, drives the group of transmit transducer elements 106 to emit ultrasonic transmit signals into a target (e.g., human, animal, underground cavity, physical structure and the like). In various embodiments, the group of transmit transducer elements 106 is operable to transmit a sequence of partially overlapping transmit beams in a plurality of directions at the target. The transmitted ultrasonic signals may be back-scattered from the target, like blood cells or tissue, to produce echoes. The echoes are received by the receive transducer elements 108.

The group of receive transducer elements 108 in the ultrasound probe 104 may be operable to convert the received echoes into analog signals, optionally undergo sub-aperture beamforming by a receive sub-aperture beamformer 116, and/or are then communicated to a receiver 118. The receiver 118 may comprise suitable logic, circuitry, interfaces and/or code that may be operable to receive the signals from the receive sub-aperture beamformer 116. The analog signals may be communicated to one or more of the plurality of A/D converters 122.

The plurality of A/D converters 122 may comprise suitable logic, circuitry, interfaces and/or code that may be operable to convert the analog signals from the receiver 118 to corresponding digital signals. The plurality of A/D converters 122 are disposed between the receiver 118 and the RF processor 124. Notwithstanding, the disclosure is not limited in this regard. Accordingly, in some embodiments, the plurality of A/D converters 122 may be integrated within the receiver 118.

The RF processor 124 may comprise suitable logic, circuitry, interfaces and/or code that may be operable to demodulate the digital signals output by the plurality of A/D converters 122. In accordance with an embodiment, the RF processor 124 may comprise a complex demodulator (not shown) that is operable to demodulate the digital signals to form I/Q data pairs that are representative of the corresponding echo signals. The RF or I/Q signal data may then be communicated to an RF/IQ buffer 126. The RF/IQ buffer 126 may comprise suitable logic, circuitry, interfaces and/or code that may be operable to provide temporary storage of the RF or I/Q signal data, which is generated by the RF processor 124.

The receive beamformer 120 may comprise suitable logic, circuitry, interfaces and/or code that may be operable to sum co-located receive data points into a pixel of a B-mode image. In various embodiments, the receive beamformer 120 applies beamforming techniques that emphasize points in space with high coherency of the delay corrected signal data. The receive beamformer 120 may be configured to replace, mix, or multiply in a measure of phase coherence into the beam sum in order to weigh down off-axis scattering signals and sidelobe energy. The beamforming techniques provided by the receive beamformer 120 may be configured to regain spatial specificity for signal data. In various embodiments, the signal data may be beamformed into a plurality of receive directions or multi-line acquisitions (MLAs) for a single transmit direction. The receive beamformer 120 may comprise suitable logic, circuitry, interfaces and/or code that may be operable to weight the delay-and-sum beamforming with a selection of coherence factors prior to IQ data summation in order to emphasize energy from reflectors in the main beam direction, and attenuate sidelobe energy from off axis scatterers. Alternative processing could also be implemented, such as minimum variance beamforming that could be combined with the output from the linear beamforming to add spatial specificity.

The receive beamformer 120 may apply various techniques for performing beamforming. For example, the receive beamformer 120 may apply a coherence factor C that measures coherence as the ratio between coherent and non-coherent summation of the delay aligned signal data, as set forth below:

$$C = \frac{\left|\sum_{i=1}^{N} x_i\right|}{\sum_{i=1}^{N} |x_i|}$$

where x is the delay aligned signal data, i is the channel number, and N is the number of channels in the beamformer. The coherence factor C is multiplied by the receive beamformer 120 in the beamformer output as a factor where tunable adjustment factors can decide to weigh the coherency in with the regular beamformer output to a large or small extent. For purposes of the present disclosure, the terms "coherence" or "coherency" are not limited to the factor C, but include any suitable methods of calculating quantities that are substantially dependent on coherence, see for example, J. Camacho et al., "Adaptive Beamforming by Phase Coherence Processing," Ultrasound Imaging, Mr. Masayuki Tanabe (Ed.), ISBN: 978-953-307-239-5, InTech, 2011, which is incorporated herein by reference in its entirety. In various embodiments, the coherency factor beamforming may be mixed with regular beamforming. The use of coherency in phase is provided to discriminate and attenuate off axis scatterers and side lobe energy from real in-beam reflectors.

In various embodiments, the resulting processed information may be co-located receive data points beam summed into a pixel of a B-mode image that is output from the receive beamformer(s) 120 and communicated to the signal processor 132. In accordance with some embodiments, the receiver 118, the plurality of A/D converters 122, the RF processor 124, and the beamformer 120 may be integrated into single beamformer(s), which may be digital. In certain embodiments, the receive beamformer(s) 120 may be multiline ultrasound beamformer(s) configured to produce multiple receive lines in response to each single transmitted beam. The multiline receive beamformer(s) 120 may apply different delays and combine the signal data to produce steered and focused receive data points. In certain embodiments, the above-mentioned beamforming techniques may be combined with other reconstruction type methods of reducing side lobe energy such as synthetic transmit beam formation or retrospective synthetic focusing techniques utilizing overlaps between two or more adjacent transmit beams. For example, the receive beamformer(s) 120 may be configured to apply Retrospective Transmit Beamforming (RTB) to provide dynamic transmit focusing and align the transmit lines with corresponding receive data points using time delays computed from a probe geometry to correct the acquired ultrasound data.

The user input device 130 may be utilized to input patient data, scan parameters, settings, select protocols and/or templates, select an imaging mode, and the like. In an exemplary embodiment, the user input device 130 may be operable to configure, manage and/or control operation of one or more components and/or modules in the ultrasound system 100. In this regard, the user input device 130 may be operable to configure, manage and/or control operation of the transmitter 102, the ultrasound probe 104, the transmit beamformer 110, the receiver 118, the receive beamformer 120, the RF processor 124, the RF/IQ buffer 126, the user input device 130, the signal processor 132, the image buffer 136, the display system 134, and/or the archive 138. The user input device 130 may include button(s), rotary encoder(s), a touchscreen, motion tracking, voice recognition, a mousing device, keyboard, camera and/or any other device capable of receiving a user directive. In certain embodiments, one or more of the user input devices 130 may be integrated into other components, such as the display system 134, for example. As an example, user input device 130 may include a touchscreen display.

The signal processor 132 may comprise suitable logic, circuitry, interfaces and/or code that may be operable to process ultrasound scan data (i.e., summed IQ signal) for generating ultrasound images for presentation on a display system 134. The signal processor 132 is operable to perform one or more processing operations according to a plurality of selectable ultrasound modalities on the acquired ultrasound scan data. In an exemplary embodiment, the signal processor 132 may be operable to perform tissue velocity image processing, speckle tracking, and the like. Acquired ultrasound scan data may be processed in real-time during a scanning session as the echo signals are received. Additionally or alternatively, the ultrasound scan data may be stored temporarily in the RF/IQ buffer 126 during a scanning session and processed in less than real-time in a live or off-line operation. In various embodiments, the processed image data can be presented at the display system 134 and/or may be stored at the archive 138. The archive 138 may be a local archive, a Picture Archiving and Communication System (PACS), or any suitable device for storing images and related information. In the representative embodiment, the signal processor 132 may comprise a measurement processor 140.

The signal processor 132 may comprise suitable logic, circuitry, interfaces and/or code that may be operable to process ultrasound scan data (i.e., summed IQ signal) for generating ultrasound images for presentation on a display system 134. The signal processor 132 is operable to perform one or more processing operations according to a plurality of selectable ultrasound modalities on the acquired ultrasound scan data. In an exemplary embodiment, the signal processor 132 may be operable to perform display processing and/or control processing, among other things. In various embodiments, the signal processor 132 may be operable to perform tissue velocity image processing, speckle tracking, and the like. Acquired ultrasound scan data may be processed in real-time during a scanning session as the echo signals are received. Additionally or alternatively, the ultrasound scan data may be stored temporarily in the RF/IQ buffer 126 during a scanning session and processed in less than real-time in a live or off-line operation. In various embodiments, the processed image data can be presented at the display system 134 and/or may be stored at the archive 138. The archive 138 may be a local archive, a Picture Archiving and Communication System (PACS), or any suitable device for storing images and related information.

The signal processor 132 may be one or more central processing units, graphic processing units, microprocessors, microcontrollers, and/or the like. The signal processor 132 may be an integrated component, or may be distributed across various locations, for example. In an exemplary embodiment, the signal processor 132 may comprise a delay compensation processor 140, a displacement determination processor 150, and a velocity information processor 160 that may be capable of receiving input information from a user input device 130 and/or archive 138, generating an output displayable by a display system 134, and manipulating the output in response to input information from a user input device 130, among other things. The signal processor 132, delay compensation processor 140, displacement determination processor 150, and velocity information processor 160 may be capable of executing any of the method(s) and/or set(s) of instructions discussed herein in accordance with the various embodiments, for example.

The ultrasound system 100 may be operable to continuously acquire ultrasound scan data at a frame rate that is suitable for the imaging situation in question. Typical frame rates range from 20-120 but may be lower or higher. The acquired ultrasound scan data may be displayed on the display system 134 at a display-rate that can be the same as the frame rate, or slower or faster. An image buffer 136 is included for storing processed frames of acquired ultrasound scan data that are not scheduled to be displayed immediately. Preferably, the image buffer 136 is of sufficient capacity to store at least several minutes' worth of frames of ultrasound scan data. The frames of ultrasound scan data are stored in a manner to facilitate retrieval thereof according to its order or time of acquisition. The image buffer 136 may be embodied as any known data storage medium.

The signal processor 132 may include a delay compensation processor 140 that comprises suitable logic, circuitry, interfaces and/or code that may be operable to compensate each receive data point from a collection of receive data points for differences in arrival times. For example, the delay compensation processor 140 may be operable to delay the receive data points to compensate for a distance between the transducer elements 106, 108 and the target. The delay alignment performed by the delay compensation processor 140 compensates for the registration differences due to transmit wave front location. The delay compensated receive data points may be provided to the receive beamformer 120 and/or stored at archive 138 or any suitable data storage medium.

Figure 2:
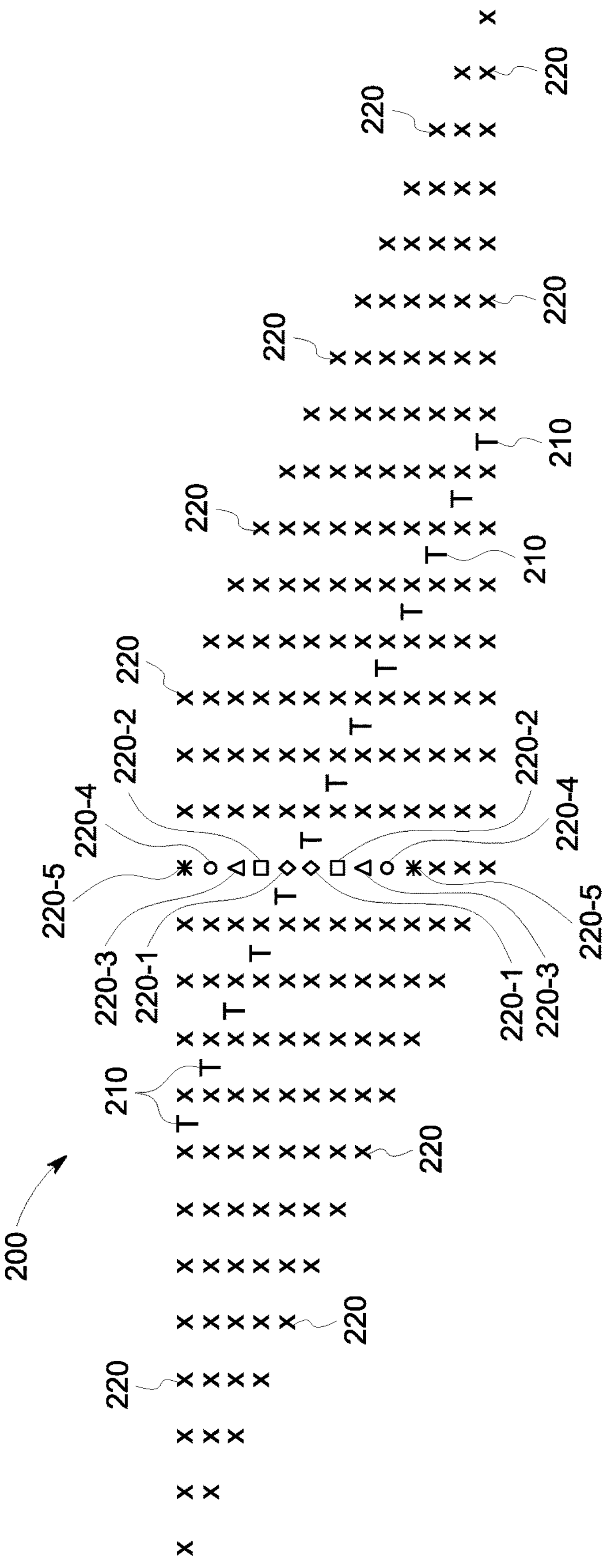
FIG. 2 is an exemplary layout of a sequence of partially overlapping transmit beams and a corresponding collection of receive data points at overlapping receive data point locations, in accordance with various embodiments.

FIG. 2 is an exemplary layout 200 of a sequence of partially overlapping transmit beams 210 and a corresponding collection of receive data points 220 at overlapping receive data point locations, in accordance with various embodiments. Referring to FIG. 2, the layout 200 may include a vertical axis corresponding with time, a horizontal axis corresponding with location/steer angle, receive data points 220 (designated by "x") for particular transmit beams 210 (designated by "T"). The sequence of overlapping transmit beams 210 are spaced out along separate transmit axes as indicated. The receive data points 220 may include pairs of co-located receive data points (e.g., 220-1, 220-2, 220-3, 220-4, 220-5, and/or any suitable pairs of co-located receive data points) generated from different transmit events 210. The identified pairs of co-located receive data points 220-1, 220-2, 220-3, 220-4, 220-5 are examples of pairs of receive data points that are suitable for calculating a correlation phase as an estimate for displacement because the identified pairs 220-1, 220-2, 220-3, 220-4, 220-5 are at receive data point locations with respect to the transmit axis that are exactly the opposite so that residual geometrical errors cancel out. The combination of the pair of co-located receive data points 220-1 provides an estimate of displacement at a pulse repetition time (PRT) difference. The combination of the pair of co-located receive data points 220-2 provides an estimate of displacement at 3*PRT difference. The combination of the pair of co-located receive data points 220-3 provides an estimate of displacement at 5*PRT difference. The combination of the pair of co-located receive data points 220-4 provides an estimate of displacement at 7*PRT difference. The combination of the pair of co-located receive data points 220-5 provides an estimate of displacement at 9*PRT difference. The different combinations of the pairs of co-located receive data points 220-1, 220-2, 220-3, 220-4, 220-5 each provide estimates at different velocity scales (e.g., pairs of co-located receive data points 220-1 and 220-2 more accurate for faster moving velocities and pairs of co-located receive data points 220-4 and 220-5 more accurate for slower moving velocities). The exemplary layout 200 may represent, for example, harmonic or fundamental transmit beams 210 emitted in different directions. The layout 200 may be generated with a high number of overlapping multi-line-acquisition (MLA) receive data point locations due to RTB processing, for example. The delay compensation processor 140 may compensate each receive data point for the different delayed arrival times of the transmit wave front at each receive pixel location. The events are thus aligned with respect to the transmit wave front but have different wave front inclination as shown in FIG. 2.

Referring again to FIG. 1 with reference to FIG. 2, the signal processor 132 may include a displacement determination processor 150 that comprises suitable logic, circuitry, interfaces and/or code that may be operable to determine a displacement of the target between transmits by comparing components of pairs of co-located receive data points 220-1, 220-2, 220-3, 220-4, 220-5 generated in response to different transmit beams 210 in the sequence of partially overlapping transmit beams 210. For example, the displacement determination processor 150 may calculate the phase of the correlation between co-located receive data points 210 after the delay compensation and perform a spatial filtering with a median filter of the estimate in order to increase signal-to-noise ratio (SNR) because a target tissue is a rigid body where neighboring pixels are moving with some degree of consistency. As an example, if $r_{x,tx}$ is data at receive location x with beam tx, then the displacement of tissue is estimated from obtaining the angle $$\phi = \text{atan}\left(r^{*}_{x,tx1} \cdot r_{x,tx2}\right)$$

and then obtaining the displacement from the angle.

In various embodiments, the displacement determination processor 150 may be configured to combine pairs of co-located receive data points 220-1, 220-2, 220-3, 220-4, 220-5 having mirrored geometrical conditions to reduce residual bias not compensated by the delay compensation processor 140. For example, the displacement determination processor 150 may be configured to combine the pair of co-located receive data points 220-1 (i.e., the innermost right-hand side MLA of one transmit to the innermost left-hand side MLA of the next transmit) to provides an estimate of displacement after 1*PRT of time. Additionally and/or alternatively, the displacement determination processor 150 may be configured to combine the pair of co-located receive data points 220-2, 220-3, 220-4, 220-5, and/or the like to provide estimates of displacement after 3*PRT, 5*PRT, 7*PRT, 9*PRT, and/or the like of time. In various embodiments, one or two of these estimates may be feasible in the vicinity of focus, whereas other combinations/estimates may be used further away from focus. In an exemplary embodiment, a large number of pairs may be combined in large parts or the entire image for a diverging, planar, or high f-number (i.e., high ratio of the imaging depth to the aperture size) transmit setup.

In certain embodiments, the displacement determination processor 150 may be configured to estimate several velocities independently at different scales by estimating individually the displacement between the proximal pair of co-located receive data points 220-1 and the more distal pairs of co-located receive data points 220-2, 220-3, 220-4, 220-5, independently, corresponding to slow tissue motion, valve motion, very rapid valve tips, or the like. In a representative embodiment, the displacement determination processor 150 may be configured to combine all correlation estimates in a total average to reduce SNR by having a larger effective packet size as set forth below:

$$\phi = \frac{\operatorname{atan}(R_{tx1,tx2})}{tx2 - tx1} + \frac{\operatorname{atan}(R_{tx4,tx3})}{tx4 - tx3} + \ldots$$

where the R indicates correlation between the data from tx1 and tx2, while the division with the number (tx2−tx1) is assuming the txN indicates the sequence number so that if tx2=tx1+3, then the division with tx2−tx1 takes into account that the displacement is 3 times as large as the PRT. The availability of longer time intervals e.g. 3*PRT or 5*PRT between the events correlated may provide a more accurate determination of velocities for slower moving events, and the use of multiple measurements in combination reduces SNR.

The signal processor 132 may include a velocity information processor 160 that comprises suitable logic, circuitry, interfaces and/or code that may be operable to generate velocity information based on the displacement of the target determined by the displacement determination processor 150. For example, the velocity information processor 160 may present the velocity information, such as color flow information or any suitable velocity information, superimposed onto a B mode image.

The archive 138 may be one or more computer-readable memories integrated with the ultrasound system 100 and/or communicatively coupled (e.g., over a network) to the ultrasound system 100, such as a Picture Archiving and Communication System (PACS), a server, a hard disk, floppy disk, CD, CD-ROM, DVD, compact storage, flash memory, random access memory, read-only memory, electrically erasable and programmable read-only memory and/or any suitable memory. The archive 138 may include databases, libraries, sets of information, or other storage accessed by and/or incorporated with the signal processor 132, for example. The archive 138 may be able to store data temporarily or permanently, for example. The archive 138 may be capable of storing medical image data, data generated by the signal processor 132, and/or instructions readable by the signal processor 132, among other things. In various embodiments, the archive 138 stores medical image data, delay compensation processing instructions, displacement determination processing instructions, target displacement estimates, velocity information processing instructions, velocity information, and beamforming instructions, for example.

The display system 134 may be any device capable of communicating visual information to a user. For example, a display system 134 may include a liquid crystal display, a light emitting diode display, and/or any suitable display or displays. The display system 134 can be operable to display information from the signal processor 132 and/or archive 138, such as B-mode images having velocity information, and/or any suitable information. In various embodiments, the display system 134 is operable to present velocity information overlaid on a B mode image.

Components of the ultrasound system 100 may be implemented in software, hardware, firmware, and/or the like. The various components of the ultrasound system 100 may be communicatively linked. Components of the ultrasound system 100 may be implemented separately and/or integrated in various forms. For example, the display system 134 and the user input device 130 may be integrated as a touchscreen display.

Figure 3:
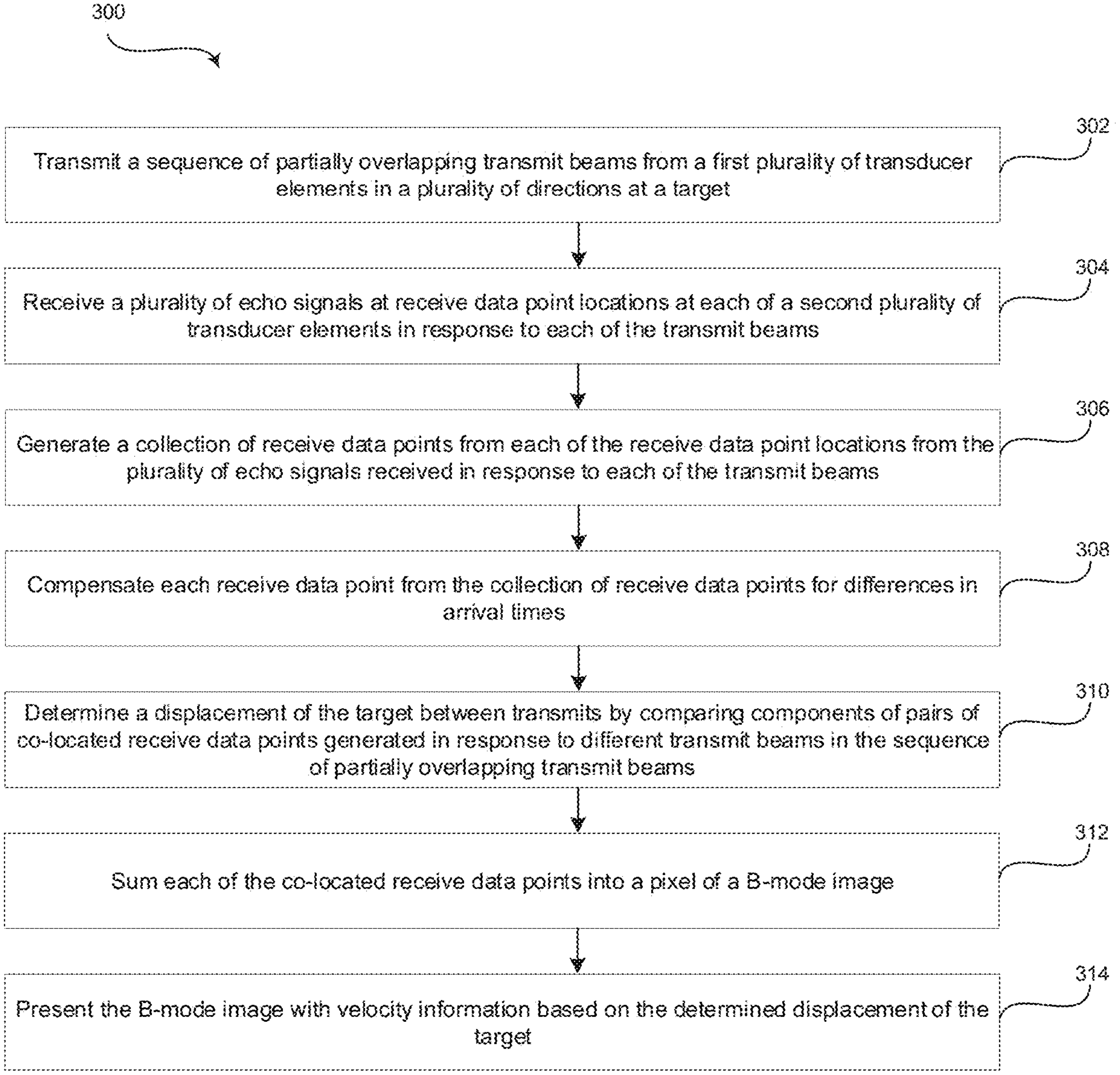
FIG. 3 is a flow chart illustrating exemplary steps for estimating motion from overlapping multiline acquisitions of successive ultrasound transmit events, in accordance with various embodiments.

FIG. 3 is a flow chart 300 illustrating exemplary steps 302-314 for estimating motion from overlapping multiline acquisitions of successive ultrasound transmit events, in accordance with various embodiments. Referring to FIG. 3, there is shown a flow chart 300 comprising exemplary steps 302 through 314. Certain embodiments may omit one or more of the steps, and/or perform the steps in a different order than the order listed, and/or combine certain of the steps discussed below. For example, some steps may not be performed in certain embodiments. As a further example, certain steps may be performed in a different temporal order, including simultaneously, than listed below.

At step 302, a sequence of partially overlapping transmit beams 210 are transmitted from a first plurality of transducer elements 106 in a plurality of directions at a target. For example, an ultrasound probe 104 having a group of transmit transducer elements 106 is positioned to acquire ultrasound data in a region of interest. The ultrasound probe transmits a sequence of transmit beams in a direction from each of the transducer elements 106. As an example, each transducer element 106 may transmit ten (10), or any suitable number, of transmit beams sequentially.

At step 304, a plurality of echo signals are received at receive data point locations at each of a second plurality of transducer elements 108 in response to each of the transmit beams 210. For example, an ultrasound probe 104 having a group of receive transducer elements 108, which normally constitute the same elements as the group of transmit transducer elements 106, receive the echo signals from the target at receive data point locations. In various embodiments, one or more of the receive data point locations of the plurality of echo signals received in response to one of the transmit beams 210 is overlapping with one or more of the receive data point locations of the plurality of echo signals received in response to one or more of other transmit beams 210 in the sequence of partially overlapping transmit beams 210.

At step 306, the ultrasound system 100 generates a collection of receive data points 220 from each of the receive data point locations from the plurality of echo signals received in response to each of the transmit beams 210. For example, an RF processor 124 of the ultrasound system 100 may generate receive data points 220 corresponding with RF signal data representative of the corresponding echo signals.

As another example, the RF processor 124 may comprise a complex demodulator that is operable to demodulate the digital signals to form the receive data points 220 corresponding with I/Q data pairs that are representative of the corresponding echo signals. The receive data points 220 may then be communicated to an RF/IQ buffer 126. The RF/IQ buffer 126 may comprise suitable logic, circuitry, interfaces and/or code that may be operable to provide temporary storage of the receive data points 220, which are generated by the RF processor 124.

At step 308, a signal processor 132 of the ultrasound system 100 compensates each receive data point 220 from the collection of receive data points 220 for differences in arrival times. For example, a delay compensation processor 140 may be configured to delay the receive data points 220 to compensate for a distance between the transducer elements 106, 108 and the target. The delay alignment performed by the delay compensation processor 140 compensates for the registration differences due to transmit wave front location.

At step 310, the signal processor 132 of the ultrasound system 100 determines a displacement of the target between transmits 210 by comparing components of pairs of co-located receive data points 220-1,220-2,220-3,220-4,220-5 generated in response to different transmit beams 210 in the sequence of partially overlapping transmit beams 210. For example, a displacement determination processor 150 of the signal processor 132 of the ultrasound system may be configured to calculate the phase of the correlation between co-located receive data points 210 after the delay compensation at step 308, and perform a spatial filtering with a median filter of the estimate in order to increase signal-to-noise ratio (SNR) because a target tissue is a rigid body where neighboring pixels are moving with some degree of consistency. As another example, the displacement determination processor 150 may be configured to combine pairs of co-located receive data points 220-1, 220-2, 220-3, 220-4, 220-5 having mirrored geometrical conditions to reduce residual bias not compensated by the delay compensation processor 140. In certain embodiments, the displacement determination processor 150 may be configured to estimate several velocities independently at different scales by estimating individually the displacement between the proximal pair of co-located receive data points 220-1 and the more distal pairs of co-located receive data points 220-2, 220-3, 220-4, 220-5, independently, corresponding to slow tissue motion, valve motion, very rapid valve tips, or the like. In a representative embodiment, the displacement determination processor 150 may be configured to combine all correlation estimates in a total average to reduce SNR by having a larger effective packet size.

At step 312, the ultrasound system 100 sums each of the co-located receive data points 220 into a pixel of a B-mode image. For example, a receive beamformer 120 of the ultrasound system 100 may be operable to combine the co-located receive data points 220 into a pixel of a B-mode image. In various embodiments, the receive beamformer 120 applies beamforming techniques that emphasize points in space with high coherency of the delay corrected signal data. The receive beamformer 120 may be configured to replace, mix, or multiply in a measure of phase coherence into the beam sum in order to weigh down off-axis scattering signals and sidelobe energy. The beamforming techniques provided by the receive beamformer 120 may be configured to regain spatial specificity for signal data. In various embodiments, the signal data may be beamformed into a plurality of receive directions or multi-line acquisitions (MLAs) for a single transmit direction. The receive beamformer 120 may comprise suitable logic, circuitry, interfaces and/or code that may be operable to weight the delay-and-sum beamforming with a selection of coherence factors prior to IQ data summation in order to emphasize energy from reflectors in the main beam direction, and attenuate sidelobe energy from off axis scatterers. Alternative processing could also be implemented, such as minimum variance beamforming that could be combined with the output from the linear beamforming to add spatial specificity. In a representative embodiment, the resulting processed information may be co-located receive data points beam summed into a pixel of a B-mode image that is output from the receive beamformer(s) 120 and communicated to the signal processor 132. In certain embodiments, the receive beamformer(s) 120 may be multiline ultrasound beamformer(s) configured to produce multiple receive lines in response to each single transmitted beam. The multiline receive beamformer(s) 120 may apply different delays and combine the signal data to produce steered and focused receive data points. In an exemplary embodiment, the above-mentioned beamforming techniques may be combined with other reconstruction type methods of reducing side lobe energy such as synthetic transmit beam formation or retrospective synthetic focusing techniques utilizing overlaps between two or more adjacent transmit beams. For example, the receive beamformer(s) 120 may be configured to apply Retrospective Transmit Beamforming (RTB) to provide dynamic transmit focusing and align the transmit beams 210 with corresponding receive data points 220 using time delays computed from a probe geometry to correct the acquired ultrasound data.

At step 314, the signal processor 132 of the ultrasound system 100 may present the B-mode image with velocity information based on the determined displacement of the target at a display system 134. For example, a velocity information processor 160 of the signal processor 132 may generate velocity information based on the displacement of the target determined by the displacement determination processor 150 at step 310. As an example, the velocity information processor 160 may present the velocity information, such as color flow information or any suitable velocity information, overlaid onto a B mode image.

Aspects of the present disclosure provide a method 300 and system 100 for estimating motion from overlapping multiline acquisitions of successive transmit events. In accordance with various embodiments, the method 300 may comprise transmitting 302, from a first plurality of transducer elements 106, a sequence of partially overlapping transmit beams 210 in a plurality of directions at a target. The method 300 may comprise receiving 304, at each of a second plurality of transducer elements 108, a plurality of echo signals at receive data point locations in response to each of the transmit beams 210. One or more of the receive data point locations of the plurality of echo signals received in response to one of the transmit beams may be overlapping with one or more of the receive data point locations of the plurality of echo signals received in response to one or more of other transmit beams 210 in the sequence of partially overlapping transmit beams 210. The method 300 may comprise generating 306, from the plurality of echo signals received in response to each of the transmit beams 210, a collection of receive data points 220 from each of the receive data point locations. The method 300 may comprise compensating 308, by at least one processor 132, 140, each receive data point 220 from the collection of receive data points 220 for differences in arrival times. The method 300 may comprise determining 310, by the at least one processor 132, 150, a displacement of the target between transmits by comparing components of pairs of co-located receive data points 220-1, 220-2, 220-3, 220-4, 220-5 generated in response to different transmit beams 210 in the sequence of partially overlapping transmit beams 210. The method 300 may comprise summing 312, by at least one beamformer 120, each of the co-located receive data points 220 into a pixel of a B-mode image. The method 300 may comprise causing 314, by the at least one processor 132, 160, a display system 134 to present the B-mode image with velocity information based on the determined displacement of the target.

In an exemplary embodiment, each of the sequence of partially overlapping transmit beams 210 is a focused transmit beam. In a representative embodiment, the method 300 may comprise selecting 310, by the at least one processor 132, 150, the pairs of co-located receive data points 220-1, 220-2, 220-3, 220-4, 220-5 exhibiting mirrored geometrical conditions with respect to corresponding locations of the different transmit beams 210 from the sequence of partially overlapping transmit beams 210. In certain embodiments, the method 300 may comprise combining 310, by the at least one processor 132, 150, the components of the pairs of co-located receive data points 220-1, 220-2, 220-3, 220-4, 220-5 exhibiting mirrored geometrical conditions from the sequence of partially overlapping transmit beams 310. In various embodiments, the displacement of the target is determined 310 by calculating a phase of a correlation between the components of the pairs of co-located receive data points 220-1, 220-2, 220-3, 220-4, 220-5. In an exemplary embodiment, the method 300 may comprise compensating 310, by the at least one processor 132, 150, each of the co-located receive data points 220 based on the determined displacement of the target. In certain embodiments, the velocity information is overlaid on the B-mode image.

Various embodiments provide an ultrasound system 100 for estimating motion from overlapping multiline acquisitions of successive transmit events. The ultrasound system 100 may comprise a plurality of transducer elements 106, 108, at least one processor 132, 140, 150, 160, at least one receive beamformer 120, and a display system 134. Each of the plurality of transducer elements 106, 108 may be operable to transmit a sequence of partially overlapping transmit beams 210 in a plurality of directions at a target and receive a collection of receive data points 220 for each of the sequence of transmit beams 210. The collection of receive data points 220 may comprise a number of receive data point locations overlapping with receive data point locations from other transmit beams 210 in the sequence of partially overlapping transmit beams 210. The at least one processor 132, 140 may be configured to compensate each receive data point 220 from the collection of receive data points 220 for a different arrival time. The at least one processor 132, 150 may be configured to determine a displacement of the target by comparing components within pairs of co-located receive data points 220-1, 220-2, 220-3, 220-4, 220-5 generated in response to different transmit beams 210 in the sequence of partially overlapping transmit beams 210. The at least one receive beamformer 120 may be operable to sum each of the co-located receive data points 220 into a pixel of a B-mode image. The display system 134 may be configured to present the B-mode image with velocity information based on the determined displacement of the target.

In a representative embodiment, each of the sequence of partially overlapping transmit beams 210 is a focused transmit beam. In various embodiments, the at least one processor 132, 150 may be configured to select the pairs of co-located receive data points 220-1, 220-2, 220-3, 220-4, 220-5 exhibiting mirrored geometrical conditions with respect to corresponding locations of the different transmit beams 210 from the sequence of partially overlapping transmit beams 210. In certain embodiments, the at least one processor 132, 150 may be configured to combine the components of the pairs of co-located receive data points 220-1, 220-2, 220-3, 220-4, 220-5 exhibiting mirrored geometrical conditions with respect to corresponding locations of the different transmit beams 210 from the sequence of partially overlapping transmit beams 210. In an exemplary embodiment, the at least one processor 132, 150 may be configured to calculate a phase of a correlation between the components of the pairs of co-located receive data points 220-1, 220-2, 220-3, 220-4, 220-5 to determine the displacement of the target. In a representative embodiment, the at least one processor 132, 150 may be configured to compensate each of the co-located receive data points 220 based on the determined displacement of the target. In various embodiments, the velocity information may be overlaid on the B-mode image.

Certain embodiments provide a non-transitory computer readable medium having stored thereon, a computer program having at least one code section. The at least one code section is executable by a machine for causing an ultrasound system 100 to perform steps 300. The steps 300 may comprise receiving 304, 306 a set of receive data points 220 for each of a sequence of partially overlapping transmit beams 210 emitted 302 from each of a plurality of transducer elements 106 in a plurality of directions at a target. The set of receive data points 220 may comprise a number of receive data point locations overlapping with receive data point locations generated from other transmit beams 210 in the sequence of partially overlapping transmit beams 210. The steps 300 may comprise compensating 308 each receive data point 220 from the set of receive data points 220 for a different arrival time. The steps 300 may comprise determining 310 a displacement of the target by comparing components of pairs of co-located receive data points 220-1, 220-2, 220-3, 220-4, 220-5 generated in response to different transmit beams 210 in the sequence of partially overlapping transmit beams 210. The steps 300 may comprise summing 312 each of the co-located receive data points 220 into a pixel of a B-mode image. The steps 300 may comprise causing 314 a display system 134 to present the B-mode image with velocity information based on the determined displacement of the target.

In various embodiments, each of the sequence of partially overlapping transmit beams 210 is a focused transmit beam. In certain embodiments, the steps 300 may comprise selecting 310 the pairs of co-located receive data points 220-1, 220-2, 220-3, 220-4, 220-5 exhibiting mirrored geometrical conditions with respect to corresponding locations of the different transmit beams 210 from the sequence of partially overlapping transmit beams 210. In an exemplary embodiment, the steps 300 may comprise combining 310 the components of the pairs of co-located receive data points 220-1, 220-2, 220-3, 220-4, 220-5 exhibiting mirrored geometrical conditions with respect to corresponding locations of the different transmit beams 210 from the sequence of partially overlapping transmit beams 210. In a preferred embodiment, the displacement of the target is determined 310 by calculating a phase of a correlation between the components of the pairs of co-located receive data points 220-1, 220-2, 220-3, 220-4, 220-5. In various embodiments, the steps 300 may comprise compensating 310 each of the co-located receive data points 220 based on the determined displacement of the target.

As utilized herein the term "circuitry" refers to physical electronic components (i.e. hardware) and any software and/or firmware ("code") which may configure the hardware, be executed by the hardware, and or otherwise be associated with the hardware. As used herein, for example, a particular processor and memory may comprise a first "circuit" when executing a first one or more lines of code and may comprise a second "circuit" when executing a second one or more lines of code. As utilized herein, "and/or" means any one or more of the items in the list joined by "and/or". As an example, "x and/or y" means any element of the three-element set {(*x*), (*y*), (x, y)}. As another example, "x, y, and/or z" means any element of the seven-element set {(*x*), (*y*), (*z*), (x, y), (x, z), (y, z), (x, y, z)}. As utilized herein, the term "exemplary" means serving as a non-limiting example, instance, or illustration. As utilized herein, the terms "e.g.," and "for example" set off lists of one or more non-limiting examples, instances, or illustrations. As utilized herein, circuitry is "operable" to perform a function whenever the circuitry comprises the necessary hardware and code (if any is necessary) to perform the function, regardless of whether performance of the function is disabled, or not enabled, by some user-configurable setting.

Other embodiments may provide a computer readable device and/or a non-transitory computer readable medium, and/or a machine readable device and/or a non-transitory machine readable medium, having stored thereon, a machine code and/or a computer program having at least one code section executable by a machine and/or a computer, thereby causing the machine and/or computer to perform the steps as described herein for estimating motion from overlapping multiline acquisitions of successive transmit events.

Accordingly, the present disclosure may be realized in hardware, software, or a combination of hardware and software. The present disclosure may be realized in a centralized fashion in at least one computer system, or in a distributed fashion where different elements are spread across several interconnected computer systems. Any kind of computer system or other apparatus adapted for carrying out the methods described herein is suited.

Various embodiments may also be embedded in a computer program product, which comprises all the features enabling the implementation of the methods described herein, and which when loaded in a computer system is able to carry out these methods. Computer program in the present context means any expression, in any language, code or notation, of a set of instructions intended to cause a system having an information processing capability to perform a particular function either directly or after either or both of the following: a) conversion to another language, code or notation; b) reproduction in a different material form.

While the present disclosure has been described with reference to certain embodiments, it will be understood by those skilled in the art that various changes may be made and equivalents may be substituted without departing from the scope of the present disclosure. In addition, many modifications may be made to adapt a particular situation or material to the teachings of the present disclosure without departing from its scope. Therefore, it is intended that the present disclosure not be limited to the particular embodiment disclosed, but that the present disclosure will include all embodiments falling within the scope of the appended claims.

What is claimed is:

1. A method comprising:

transmitting, from a first plurality of transducer elements, a sequence of partially overlapping transmit beams in a plurality of directions at a target;

receiving, at each of a second plurality of transducer elements, a plurality of echo signals at receive data point locations in response to each of the transmit beams, wherein one or more of the receive data point locations of the plurality of echo signals overlap with one or more of the receive data point locations of the plurality of echo signals from different transmit beams in the sequence of partially overlapping transmit beams;

generating, from the plurality of echo signals received in response to each of the transmit beams, a collection of receive data points from each of the receive data point locations;

compensating, by at least one processor, each receive data point from the collection of receive data points for differences in arrival times;

determining, by the at least one processor, a displacement of the target between transmits by comparing components of pairs of co-located receive data points generated in response to the different transmit beams in the sequence of partially overlapping transmit beams;

summing, by at least one beamformer, each of the co-located receive data points into a pixel of a B-mode image; and causing, by the at least one processor, a display system to present the B-mode image with velocity information based on the determined displacement of the target.

2. The method of claim 1, wherein each of the sequence of partially overlapping transmit beams is a focused transmit beam.

3. The method of claim 1, comprising selecting, by the at least one processor, the pairs of co-located receive data points exhibiting mirrored geometrical conditions with respect to corresponding locations of the different transmit beams from the sequence of partially overlapping transmit beams.

4. The method of claim 1, comprising combining, by the at least one processor, the components of the pairs of co-located receive data points exhibiting mirrored geometrical conditions from the sequence of partially overlapping transmit beams.

5. The method of claim 1, wherein the displacement of the target is determined by calculating a phase of a correlation between the components of the pairs of co-located receive data points.

6. The method of claim 1, comprising compensating, by the at least one processor, each of the co-located receive data points based on the determined displacement of the target.

7. The method of claim 1, wherein the velocity information is overlaid on the B-mode image.

8. An ultrasound system comprising:

a plurality of transducer elements, wherein each of the plurality of transducer elements is operable to:

transmit a sequence of partially overlapping transmit beams in a plurality of directions at a target;

receive a collection of receive data points for each of the sequence of transmit beams, wherein the collection of receive data points comprises a number of receive data point locations overlapping with receive data point locations from different transmit beams in the sequence of partially overlapping transmit beams;

at least one processor configured to:

compensate each receive data point from the collection of receive data points for a different arrival time; and determine a displacement of the target by comparing components within pairs of co-located receive data points generated in response to the different transmit beams in the sequence of partially overlapping transmit beams;

at least one receive beamformer operable to sum each of the co-located receive data points into a pixel of a B-mode image; and a display system configured to present the B-mode image with velocity information based on the determined displacement of the target.

9. The system of claim 8, wherein each of the sequence of partially overlapping transmit beams is a focused transmit beam.

10. The system of claim 8, wherein the at least one processor is configured to select the pairs of co-located receive data points exhibiting mirrored geometrical conditions with respect to corresponding locations of the different transmit beams from the sequence of partially overlapping transmit beams.

11. The system of claim 8, wherein the at least one processor is configured to combine the components of the pairs of co-located receive data points exhibiting mirrored geometrical conditions with respect to corresponding locations of the different transmit beams from the sequence of partially overlapping transmit beams.

12. The system of claim 8, wherein the at least one processor is configured to calculate a phase of a correlation between the components of the pairs of co-located receive data points to determine the displacement of the target.

13. The system of claim 8, wherein the at least one processor is configured to compensate each of the co-located receive data points based on the determined displacement of the target.

14. The system of claim 8, wherein the velocity information is overlaid on the B-mode image.

15. A non-transitory computer readable medium having stored thereon, a computer program having at least one code section, the at least one code section being executable by a machine for causing an ultrasound system to perform steps comprising:

receiving a set of receive data points for each of a sequence of partially overlapping transmit beams emitted from each of a plurality of transducer elements in a plurality of directions at a target, wherein the set of receive data points comprises a number of receive data point locations overlapping with receive data point locations generated from different transmit beams in the sequence of partially overlapping transmit beams;

compensating each receive data point from the set of receive data points for a different arrival time;

determining a displacement of the target by comparing components of pairs of co-located receive data points generated in response to the different transmit beams in the sequence of partially overlapping transmit beams;

summing each of the co-located receive data points into a pixel of a B-mode image; and causing a display system to present the B-mode image with velocity information based on the determined displacement of the target.

16. The non-transitory computer readable medium of claim 15, wherein each of the sequence of partially overlapping transmit beams is a focused transmit beam.

17. The non-transitory computer readable medium of claim 15, wherein the steps comprise selecting the pairs of co-located receive data points exhibiting mirrored geometrical conditions with respect to corresponding locations of the different transmit beams from the sequence of partially overlapping transmit beams.

18. The non-transitory computer readable medium of claim 15, wherein the steps comprise combining the components of the pairs of co-located receive data points exhibiting mirrored geometrical conditions with respect to corresponding locations of the different transmit beams from the sequence of partially overlapping transmit beams.

19. The non-transitory computer readable medium of claim 15, wherein the displacement of the target is determined by calculating a phase of a correlation between the components of the pairs of co-located receive data points.

20. The non-transitory computer readable medium of claim 15, wherein the steps comprise compensating each of the co-located receive data points based on the determined displacement of the target.

* * * * *